(12) United States Patent
Noda et al.

(10) Patent No.: US 10,267,735 B2
(45) Date of Patent: Apr. 23, 2019

(54) SURFACE PLASMON-FIELD ENHANCED FLUORESCENCE DETECTION DEVICE

(71) Applicant: KONICA MINOLTA, INC., Tokyo (JP)

(72) Inventors: Tetsuya Noda, Tokyo (JP); Fumio Nagai, Tokyo (JP); Nobuhiro Yamauchi, Tokyo (JP); Yuichi Kyogoku, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/558,526

(22) PCT Filed: Mar. 8, 2016

(86) PCT No.: PCT/JP2016/057048
§ 371 (c)(1),
(2) Date: Sep. 14, 2017

(87) PCT Pub. No.: WO2016/147937
PCT Pub. Date: Sep. 22, 2016

(65) Prior Publication Data
US 2018/0080873 A1    Mar. 22, 2018

(30) Foreign Application Priority Data
Mar. 17, 2015    (JP) ................. 2015-053467

(51) Int. Cl.
*G01N 21/64*    (2006.01)
*G01N 21/552*    (2014.01)

(52) U.S. Cl.
CPC .......... *G01N 21/648* (2013.01); *G01N 21/64* (2013.01); *G01N 21/6428* (2013.01);
(Continued)

(58) Field of Classification Search
CPC .. G01N 21/648; G01N 21/64; G01N 21/6428; G01N 21/553; G01N 2021/6463;
(Continued)

(56) References Cited

U.S. PATENT DOCUMENTS 3,881,826 A * 5/1975 De Leeuw ............. G01N 21/05
250/576
5,421,337 A * 6/1995 Richards-Kortum ........
A61B 5/0071
600/477

(Continued)

FOREIGN PATENT DOCUMENTS

EP    2579023 A1    4/2013
EP    2905617       8/2015
(Continued)

OTHER PUBLICATIONS

European Patent Application No. 16764767.6; Extended Search Report; dated Jan. 5, 2018; 13 pages.
(Continued)

*Primary Examiner* — David P Porta
*Assistant Examiner* — Blake C Riddick

(57) ABSTRACT

This detection device has a holder, light irradiation unit, angle adjustment unit, light receiving sensor, light receiving optical system, optical filter, and a control unit. The light receiving optical system guides light from a detection chip to the light receiving sensor. The optical filter is disposed in the light receiving optical system, blocks a part of plasmon scattered light, and passes, out of the light emitted from the detection chip, a part of the plasmon scattered light, and fluorescence emitted from a fluorescent material. The light receiving sensor detects the fluorescent light, and the part of the plasmon scattered light, which have been emitted from the detection chip and passed the optical filter. On the basis of the detection results of the plasmon scattered light, the
(Continued)

control unit controls the angle adjustment unit, and adjusts the incident angle of the excitation light to a predetermined incident angle.

7 Claims, 5 Drawing Sheets

(52) U.S. Cl.
 CPC ... *G01N 21/553* (2013.01); *G01N 2021/6463* (2013.01); *G01N 2021/6471* (2013.01); *G01N 2201/0638* (2013.01); *G01N 2201/0806* (2013.01)

(58) Field of Classification Search
 CPC ... G01N 2021/6471; G01N 2201/0638; G01N 2201/0806
 USPC .......................................... 250/458.1, 459.1
 See application file for complete search history.

(56) References Cited

U.S. PATENT DOCUMENTS

| | | | | |
|---|---|---|---|---|
| 2007/0049809 A1* | 3/2007 | Bechtel | ............. | A61B 5/14532 600/316 |
| 2012/0196385 A1* | 8/2012 | Yamamoto | ......... | G01N 21/6428 436/529 |
| 2012/0201716 A1* | 8/2012 | Matsuo | ................ | G01N 21/553 422/69 |
| 2013/0078146 A1* | 3/2013 | Sando | .................. | G01N 21/648 422/69 |
| 2013/0078148 A1* | 3/2013 | Kaya | .................... | G01N 21/648 422/69 |
| 2013/0143332 A1* | 6/2013 | Tsukagoshi | ............ | G01N 21/05 436/501 |
| 2013/0175457 A1 | 7/2013 | Wada | | |
| 2014/0061506 A1* | 3/2014 | Kaya | ................. | G01N 21/6428 250/459.1 |
| 2016/0153910 A1* | 6/2016 | Fujii | .................... | G01N 21/648 436/501 |

FOREIGN PATENT DOCUMENTS

| | | |
|---|---|---|
| JP | 10-307141 A | 11/1998 |
| JP | 2009-128152 A | 6/2009 |
| JP | 2013-057580 A | 3/2013 |
| JP | 2013-238611 A | 11/2013 |
| WO | 2011/152064 A1 | 12/2011 |
| WO | 2012/042807 A1 | 4/2012 |
| WO | 2014/054389 | 4/2014 |
| WO | 2015/008492 A1 | 1/2015 |

OTHER PUBLICATIONS

Official Action issued in corresponding EP Application No. 16764767.6 dated Oct. 30, 2018.

* cited by examiner

SURFACE PLASMON-FIELD ENHANCED FLUORESCENCE DETECTION DEVICE

CROSS-REFERENCE TO RELATED APPLICATIONS

This application is a National Stage of International patent application PCT/JP2016/057048, filed on Mar. 8, 2016, which claims priority to foreign Japanese patent application No. JP 2015-053467, filed on Mar. 17, 2015, the disclosures of which are incorporated by reference in their entirety.

TECHNICAL FIELD

The present invention relates to a detection device for detecting a detection object substance in a sample.

BACKGROUND ART

Highly sensitive and quantitative detection of a minute amount of a detection object substance such as protein and DNA in laboratory tests makes it possible to perform treatment by quickly determining the patient's condition. There is therefore a need for a detection device which can quantitatively measure a minute amount of detection object substance with high sensitivity.

Surface plasmon-field enhanced fluorescence spectroscopy (hereinafter abbreviated as "SPFS") is known as a method which can detect a detection object substance with high sensitivity (see, for example, PTLS 1 and 2).

PTLS 1 and 2 disclose detection devices which utilize SPFS. In the detection devices disclosed in PTLS 1 and 2, a detection chip including a prism made of a dielectric, a metal film formed on one surface of the prism, and a capturing body (for example antibody) fixed on the metal film is used. When a sample containing a detection object substance is provided on the metal film, the detection object substance is captured by the capturing body (primary reaction). The detection object substance thus captured is further labeled by a fluorescence material (secondary reaction). In this state, when excitation light is applied to the prism through the metal film at an angle at which surface plasmon resonance is caused, localized-field light can be generated on the surface of the metal film. With this localized-field light, the fluorescence material for labelling the captured detection object substance on the metal film is selectively excited, and fluorescence is emitted from the fluorescence material. In the detection devices, the fluorescence is detected to detect the presence or the amount of the detection object sub stance.

In such detection devices utilizing SPFS, it is necessary to use highly sensitive light sensors such as a photomultiplier tube (PMT) and an avalanche photodiode (APD) to quantitatively detect weak fluorescence.

CITATION LIST

Patent Literature

PTL 1
Japanese Patent Application Laid-Open No. 10-307141
PTL 2
WO2012/042807

SUMMARY OF INVENTION

Technical Problem

In detection devices utilizing SPFS, it is necessary to set the incident angle of the excitation light to the metal film such that the fluorescence intensity is maximized for the purpose of sufficiently improving the detection sensitivity and the detection accuracy.

The detection device disclosed in PTL 1 applies excitation light at an incident angle at which the intensity of the reflection light from the metal film is minimized (hereinafter referred to as "resonance angle"). However, since the resonance angle and the incident angle at which the intensity of fluorescence light is maximized are slightly different from each other, the detection device disclosed in PTL 1 has a room for improvement in detection sensitivity and detection accuracy.

In the detection device disclosed in PTL 2, excitation light is applied at an incident angle at which the intensity of diffusing light generated by surface plasmon resonance (hereinafter referred to as "plasmon scattering light") is maximized (hereinafter referred to as "enhancement angle"). Since the enhancement angle is closer to the incident angle at which the intensity of the fluorescence light is maximized than the resonance angle, the detection device disclosed in PTL 2 are more advantageous than the detection device disclosed in PTL 1 in terms of detection sensitivity and detection accuracy. In the detection device disclosed in PTL 2, however, the light receiving sensor for detecting fluorescence is used also for detecting the plasmon scattering light, and disadvantageously the excitation light cutting filter (optical filter) has to be moved out from the light path of the light reception optical system at the time of determining the enhancement angle.

An object of the present invention is to provide a detection device which can determine, without moving out the optical filter from the light path of the light reception optical system, the enhancement angle at which the plasmon scattering light is maximized.

Solution to Problem

To solve the above-mentioned problems, a detection device according to an embodiment of the present invention is configured to, in a state where a detection chip including a prism composed of a dielectric and a metal film disposed on one surface of the prism is placed in the detection device, apply excitation light to the metal film through the prism to excite a fluorescence material for labelling a detection object substance on the metal film with localized light based on surface plasmon resonance, and detect fluorescence emitted from the fluorescence material to detect presence or an amount of the detection object substance, the detection device including: a holder configured to hold the detection chip; a light irradiation section configured to emit the excitation light; an angle adjusting section configured to adjust an incident angle of the excitation light to the metal film to apply the excitation light to the metal film through the prism at a predetermined incident angle; a light receiving sensor configured to detect light emitted from the detection chip when the light irradiation section applies the excitation light to the metal film; a light reception optical system configured to guide light emitted from the detection chip to the light receiving sensor; an optical filter disposed in the light reception optical system, and configured to block a part of plasmon scattering light having a wavelength identical to a wavelength of the excitation light; and a control section configured to control the angle adjusting section. The optical filter allows a part of the plasmon scattering light and fluorescence emitted from the fluorescence material in the light emitted from the detection chip to pass therethrough, the light receiving sensor detects a part of the plasmon scattering light from the detection chip which has passed through the optical filter when the light irradiation section applies the excitation light to the metal film in a state where the fluorescence material is not present on the metal film, on a basis of a detection result of the plasmon scattering light of the light receiving sensor, the control section determines the predetermined incident angle, and controls the angle adjusting section to adjust an incident angle of the excitation light to the metal film to the predetermined incident angle, and the light receiving sensor detects fluorescence emitted from the fluorescence material when the light irradiation section applies the excitation light to the metal film at the predetermined incident angle in a state where the detection object substance labeled with the fluorescence material is present on the metal film such that a surface plasmon resonance is generated on the metal film.

Advantageous Effects of Invention

According to the present invention, during detection of a detection object substance by use of SPFS, the enhancement angle at which the plasmon scattering light is maximized can be determined without moving out the optical filter from the light path of the light reception optical system. Therefore, according to the present invention, the presence or the amount of a detection object substance can be detected with high sensitivity, high accuracy and high speed. Moreover, according to the present invention, downsizing and cost reduction of the detection device can be achieved.

DESCRIPTION OF EMBODIMENTS

Embodiments of the present invention are described in detail below with reference to the accompanying drawings.

Embodiment 1

(Configuration of Detection Device)

First, a surface plasmon resonance fluorescence analysis device (hereinafter also referred to as "SPFS device") is described as a typical example of a detection device according to Embodiment 1 of the present invention.

Figure 1:
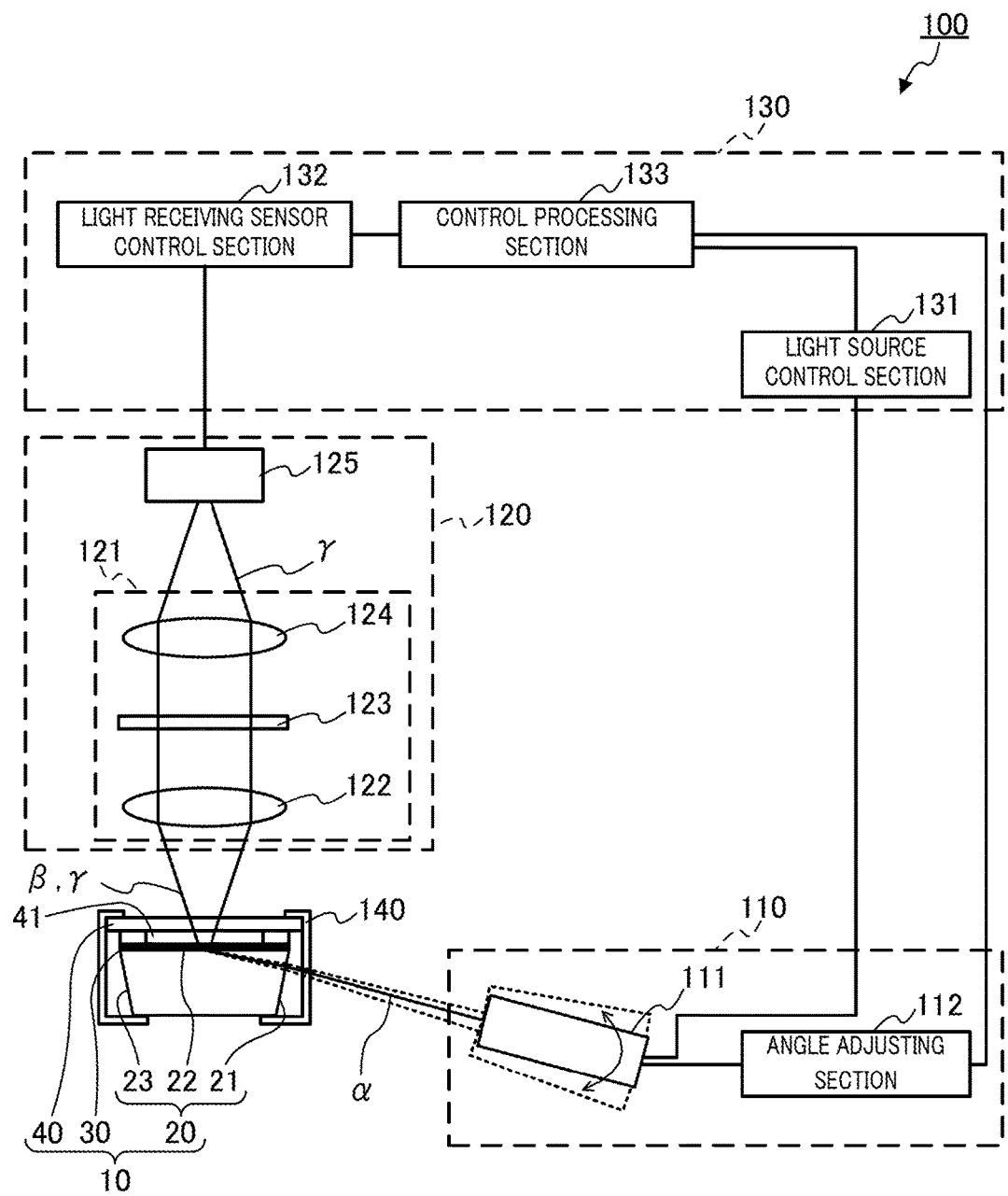
FIG. 1 is a schematic view illustrating a configuration of an SPFS device according to Embodiment 1.

FIG. 1 is a schematic view illustrating a configuration of SPFS device 100 according to Embodiment 1. As illustrated in FIG. 1, SPFS device 100 includes excitation light irradiation unit (light irradiation section) 110 for applying excitation light α to detection chip 10, light reception unit 120 for detecting light (plasmon scattering light β and fluorescence γ) emitted from detection chip 10, control section 130 that controls the units, chip holder 140 for detachably holding detection chip 10, and a liquid feeding unit (not illustrated in the drawing) for feeding liquid to detection chip 10. SPFS device 100 is used with detection chip 10 placed in chip holder 140. For such a configuration, detection chip 10 is described first, and thereafter the components of SPFS device 100 are described.

As illustrated in FIG. 1, detection chip 10 includes prism 20 having incidence surface 21, film formation surface 22 and emission surface 23, metal film 30 formed on film formation surface 22, and channel closure 40 disposed on film formation surface 22 or metal film 30. Normally, detection chip 10 is replaced for each detection. Detection chip 10 is preferably a structure with each side of several millimeters to several centimeters, but may also be a smaller structure or a larger structure which are not categorized as "chip."

Prism 20 is a dielectric which is transparent to excitation light α. Prism 20 includes incidence surface 21, film formation surface 22 and emission surface 23. Incidence surface 21 is a surface through which excitation light α from excitation light irradiation unit 110 enters prism 20. Metal film 30 is formed on film formation surface 22. Excitation light α having entered prism 20 is reflected by metal film 30. To be more specific, the excitation light α having entered prism 20 is reflected by the interface (film formation surface 22) between prism 20 and metal film 30. Emission surface 23 is a surface through which excitation light α reflected by metal film 30 is emitted out of prism 20.

The shape of prism 20 is not limited. In the present embodiment, the shape of prism 20 is a column whose bottom surface is a trapezoid. The surface corresponding to a bottom side of the trapezoid is film formation surface 22. The surface corresponding to one leg is incidence surface 21, and the surface corresponding to the other leg is emission surface 23. Preferably, the trapezoid serving as the bottom surface is an isosceles trapezoid. With such a configuration, incidence surface 21 and emission surface 23 are symmetrical, and the S wave component of excitation light α does not easily remain in prism 20. Incidence surface 21 is formed such that excitation light α does not return to excitation light irradiation unit 110. The reason for this is that, if excitation light α returns to the laser diode serving as the excitation light source, the excitation state of the laser diode is disturbed, and the wavelength and the output of the excitation light α is varied. In view of this, the angle of incidence surface 21 is set within a scanning range around the ideal enhancement angle such that that excitation light α is not perpendicularly incident on incidence surface 21. For example, the angle between incidence surface 21 and film formation surface 22, and the angle between film formation surface 22 and emission surface 23 are each approximately 80 degrees.

Examples of the material of prism 20 include a resin and a glass. Preferably, the material of prism 20 is a resin which has a refractive index of 1.4 to 1.6 and causes only a small birefringence and autofluorescence.

Metal film 30 is formed on film formation surface 22 of prism 20. When metal film 30 is provided, interaction (surface plasmon resonance) is caused between the photon of excitation light α which is incident on film formation surface 22 under the total reflection condition and the free electron in metal film 30, and thus localized-field light can be generated on the surface of metal film 30. The material of metal film 30 is not limited as long as surface plasmon resonance can be caused. Examples of the material of metal film 30 include gold, silver, copper, aluminum, and their alloys. In the present embodiment, metal film 30 is a thin film made of gold. The formation method for metal film 30 is not limited. Examples of the formation method for metal film 30 include sputtering, deposition, and plating. Preferably, the thickness of metal film 30 is, but not limited to, 30 to 70 nm.

In addition, although not illustrated in FIG. 1, a capturing body for capturing the detection object substance is fixed on the surface of metal film 30 on the side facing away from prism 20. With this configuration, a detection region for selectively detecting the detection object substance can be formed. The type of the capturing body is not limited as long as the detection object substance can be captured. For example, the capturing body is an antibody which can be specifically coupled with the detection object substance, or a fragment of the antibody.

Channel closure 40 is disposed on the surface of metal film 30 that faces away from prism 20 with channel 41 interposed therebetween. When metal film 30 is partly formed on film formation surface 22 of prism 20, channel closure 40 may be disposed on film formation surface 22 with channel 41 interposed therebetween. Together with metal film 30 (and prism 20), channel closure 40 forms flow channel 41 through which liquid such as a sample, fluorescence labeling solution, and washing solution flows. The capturing body is exposed to the interior of channel 41. Both ends of channel 41 are respectively connected to the inlet and outlet (both omitted in the drawing) formed on the top surface of channel closure 40. When liquid is injected into channel 41, the liquid makes contact with the capturing body in channel 41. Channel closure 40 is made of a material transparent to light (plasmon scattering light $\beta$ and fluorescence $\gamma$) emitted from the surface of metal film 30 that faces away from prism 20 and from the area in the vicinity of the surface of metal film 30. Examples of the material of channel closure 40 include a resin. As long as the above-mentioned light can be guided to light reception unit 120, channel closure 40 may be partly made of an opaque material. Channel closure 40 is joined to metal film 30 or prism 20 by bonding using a double-sided tape or an adhesive agent, laser welding, ultrasound welding, or pressure fixing using a clamping member, for example.

As illustrated in FIG. 1, excitation light $\alpha$ guided to prism 20 enters prism 20 from incidence surface 21. The excitation light $\alpha$ having entered prism 20 is incident on the interface (film formation surface 22) between prism 20 and metal film 30 at a total reflection angle (at an angle that causes surface plasmon resonance). The reflection light from the interface is emitted out of prism 20 from emission surface 23 (which is not illustrated in the drawing). Meanwhile, when excitation light $\alpha$ is incident on the interface at an angle that causes surface plasmon resonance, plasmon scattering light $\beta$ and fluorescence $\gamma$ are emitted from metal film 30 and the area in the vicinity of metal film 30 in the direction toward light reception unit 120. In addition, autofluorescence is emitted from the resin member (prism 20) of detection chip 10 (which is not illustrated in the drawing).

Next, the components of SPFS device 100 are described. As described above, SPFS device 100 includes excitation light irradiation unit (light irradiation section) 110, light reception unit 120, control section 130 and chip holder (holder) 140.

Excitation light irradiation unit 110 includes light source unit 111 that emits excitation light $\alpha$, and angle adjusting section 112 that adjusts the incident angle of excitation light $\alpha$ to the interface (film formation surface 22) between prism 20 and metal film 30.

Light source unit 111 includes the light source of excitation light $\alpha$, and emits excitation light $\alpha$ (single mode laser light) toward incidence surface 21 of detection chip 10 held by chip holder 140. To be more specific, light source unit 111 emits only P wave with respect to the interface (film formation surface 22) between prism 20 and metal film 30 of detection chip 10 toward incidence surface 21 such that the angle of excitation light $\alpha$ to the interface is a total reflection angle.

While the type of the light source is not limited, the light source preferably has a high power in the case where a light detector which does not have high sensitivity such as a photodiode (PD) is used as light receiving sensor 125 from the viewpoint of increasing the light reception amount of light receiving sensor 125. The light source is, for example, a laser diode (LD) capable of emitting excitation light $\alpha$ such that the power of the irradiated surface on metal film 30 is 1 m W/mm$^2$ or greater. With this configuration, highly intense fluorescence $\gamma$ can be emitted from the fluorescence material that labels the detection object substance. In addition, preferably, the wavelength of excitation light $\alpha$ emitted by the LD is, but not limited to, 650 to 670 nm, for example. Other examples of the type of the light source include a light-emitting diode, a mercury lamp, and other laser light sources.

In addition, in the case where excitation light $\alpha$ emitted from the light source is not a beam, the excitation light $\alpha$ is converted to a beam by a lens, a mirror, a slit or the like. In addition, in the case where excitation light $\alpha$ emitted from the light source is not monochromatic light, the excitation light $\alpha$ is converted to monochromatic light by a diffraction grid or the like. Further, in the case where excitation light $\alpha$ emitted from the light source is not linear polarization, the excitation light $\alpha$ is converted to light of linear polarization by a polarizer or the like.

In addition, light source unit 111 further includes a shaping optical system, an APC mechanism and a temperature adjusting mechanism (which are not illustrated in the drawing).

The shaping optical system adjusts the beam diameter, the outline shape and the like of excitation light $\alpha$ such that the irradiation spot on the interface (film formation surface 22) between prism 20 and metal film 30 has a circular shape of a predetermined size. The excitation light $\alpha$ emitted from the shaping optical system is applied to prism 20 of detection chip 10. The beam shaping optical system includes a collimator, a band pass filter (BPF), a linear polarization filter (LPF), a half-wave plate, a slit, a zooming unit and the like, for example.

The collimator collimates excitation light $\alpha$ emitted from the light source.

The band pass filter changes excitation light $\alpha$ emitted from the light source to narrowband light composed only of a central wavelength. The reason for this is that excitation light $\alpha$ from the light source has a slight wavelength distribution width.

The linear polarization filter changes excitation light $\alpha$ emitted from the light source to linearly polarized light. The half-wave plate adjusts the polarization direction of excitation light $\alpha$ such that light of the P wave component is incident on metal film 30. The slit and the zooming unit adjust the beam diameter, the outline shape and the like of excitation light $\alpha$ such that the shape of the irradiation spot on the rear surface of metal film 30 has a circular shape of a predetermined size.

The APC mechanism controls the light source such that the output of the light source is maintained at a constant value. To be more specific, the APC mechanism detects the quantity of the light diverged from excitation light $\alpha$ by a photodiode not illustrated and the like. Then, the APC mechanism controls the input energy by a recurrent circuit to control the output of the light source at a constant value.

The temperature adjusting mechanism is composed of a heater, a Peltier device, or the like, for example. The wavelength and the energy of the light emitted from the light source can be varied by the temperature. Therefore, the temperature of the light source is maintained at a constant value by the temperature adjusting mechanism to control the wavelength and the energy of the light emitted from the light source at a constant value.

Angle adjusting section 112 adjusts the incident angle of excitation light α to metal film 30 (film formation surface 22). Angle adjusting section 112 relatively rotates the optical axis of excitation light α and the chip holder to apply excitation light α to a predetermined position of metal film 30 (film formation surface 22) through prism 20 at a predetermined incident angle. In the present embodiment, angle adjusting section 112 rotates light source unit 111 about the axis orthogonal to the optical axis of excitation light α. At this time, the position of the rotation axis is set such that the irradiation position on metal film 30 (film formation surface 22) is not substantially moved when the incident angle is scanned. For example, by setting the position of the rotation center at a position near the intersection of the optical axes of two rays of excitation light α at both ends of the scanning range of the incident angle (at a position between the irradiation position on film formation surface 22 and incidence surface 21), the shift of the irradiation position can be minimized.

Light reception unit 120 is disposed to face the surface of metal film 30 facing away from prism 20 in detection chip 10 held by chip holder 140. To be more specific, light reception unit 120 is disposed such that first lens 122, second lens 124 and light reception sensor 125 described later are located on a straight line that passes through the irradiation spot of excitation light α on metal film 30 (film formation surface 22) and is perpendicular to the surface of metal film 30. Light reception unit 120 detects the light (plasmon scattering light β, fluorescence γ and autofluorescence) emitted from detection chip 10. Light reception unit 120 includes light reception optical system 121 including first lens 122, excitation light cutting filter 123 and second lens 124, and light receiving sensor 125. Light reception optical system 121 guides the light emitted from detection chip 10 to light receiving sensor 125.

First lens 122 and second lens 124 form a conjugate optical system that is not easily influenced by stray light. The light rays that travel between first lens 122 and second lens 124 are substantially parallel light. First lens 122 and second lens 124 form an image of the light emitted from detection chip 10 on the light reception surface of light reception sensor 125. In addition, as described later, first lens 122 and second lens 124 collect, at the light reception surface of light receiving sensor 125, the light (plasmon scattering light β, fluorescence γ and autofluorescence) emitted from detection chip 10 together with excitation light cutting filter 123.

Excitation light cutting filter (optical filter) 123 is disposed between first lens 122 and second lens 124. Excitation light cutting filter 123 blocks a part (a large part) of the light (plasmon scattering light β) having a wavelength same as excitation light α. On the other hand, in the light emitted from detection chip 10, excitation light cutting filter 123 allows a part of plasmon scattering light β and fluorescence γ emitted from the fluorescence material to pass therethrough. In the present embodiment, excitation light cutting filter 123 also allows at least a part of the autofluorescence emitted from detection chip 10 to pass therethrough. As will be described in detail later, with this configuration, SPFS device 100 can detect the detection object substance with high accuracy by removing large part of plasmon scattering light β which becomes a noise component in detection of fluorescence γ, and can determine the enhancement angle by detecting the transmitted plasmon scattering light β with light receiving sensor 125 without moving out excitation light cutting filter 123. While the transmittance of plasmon scattering light β of excitation light cutting filter 123 is not limited as long as the above-mentioned effects can be obtained, the transmittance of plasmon scattering light β of excitation light cutting filter 123 is preferably greater than 0.005% and smaller than 1%. In addition, preferably, excitation light cutting filter 123 allows plasmon scattering light β to pass therethrough such that the quantity of plasmon scattering light β is greater than 0.5 times and smaller than 100 times the quantity of the autofluorescence emitted from detection chip 10.

Examples of the type of excitation light cutting filter 123 include a reflection filter having a dielectric multi-layer film disposed on one surface or both surfaces thereof. The dielectric multi-layer film can be formed by alternately laminating a layer made of a high refractive index material and a layer made of a low refractive index material. By appropriately setting the thickness and the number of the layers and the like in the formation of the film, a filter having desired transmission characteristics can be obtained. Examples of the high refractive index material include oxides of Ti, Nb, Ta, La and the like (for example, $TiO_2$, $Nb_2O_5$, $Ta_2O_5$ and the like). Examples of the low refractive index material include oxides of Si, Al and the like (for example, $SiO_2$ and the like). For example, excitation light cutting filter 123 can be produced by alternately laminating a $Nb_2O_5$ layer (having a thickness of approximately 100 nm) and a $SiO_2$ layer (having a thickness of approximately 100 nm) until 40 to 50 layers are laminated on the surface of a glass substrate (BK7) to form a dielectric multi-layer film (having a thickness of 4000 to 5000 nm). With excitation light cutting filter 123 obtained in the above-mentioned manner, the reflectivity of light having a wavelength (for example, 660 nm) same as the wavelength of excitation light α is 99% or higher, and the reflectivity of light having a wavelength (for example, 690 nm) greater than the wavelength of excitation light α by 30 nm is several % or lower, in the case where the incident angle of the main light beam to the filter is 0 degree.

Examples of excitation light cutting filter 123 further includes an absorption filter made of color glass. In general, regarding the transmission spectrum of an absorption filter, it is difficult to sharply increase the transmittance in the vicinity of the cut-off wavelength (the wavelength of the boundary between the wavelength band where excitation light α is absorbed by excitation light cutting filter 123 and the wavelength band where excitation light α is allowed to pass therethrough). In view of this, the performance of shielding excitation light α of a transmission filter is lower than that of a reflection filter. However, in SPFS device 100 according to the present embodiment, excitation light cutting filter 123 allows a part of plasmon scattering light β to pass therethrough. With this configuration, SPFS device 100 according to the present embodiment can use an inexpensive color glass filter although the light-shielding performance is low.

Light receiving sensor 125 detects the light emitted from detection chip 10. Examples of the type of light receiving sensor 125 include an avalanche photodiode (APD) and a photomultiplier tube (PMT) having high sensitivity and S/N ratio. In the case where a high-power light source is used, a photodiode (PD) which does not have high sensitivity and the like may be used as light receiving sensor 125. From a view point of the cost reduction the downsizing of SPFS device 100, use of a PD is preferable.

Figure 2A:
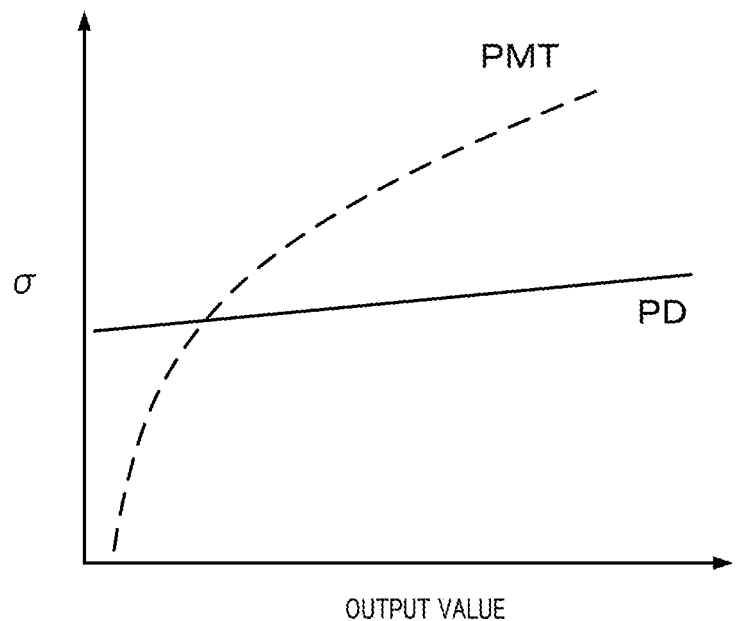
FIGS. 2A and 2B are conceptual graphs showing detection accuracies of a PMT and a PD.
Figure 2B:
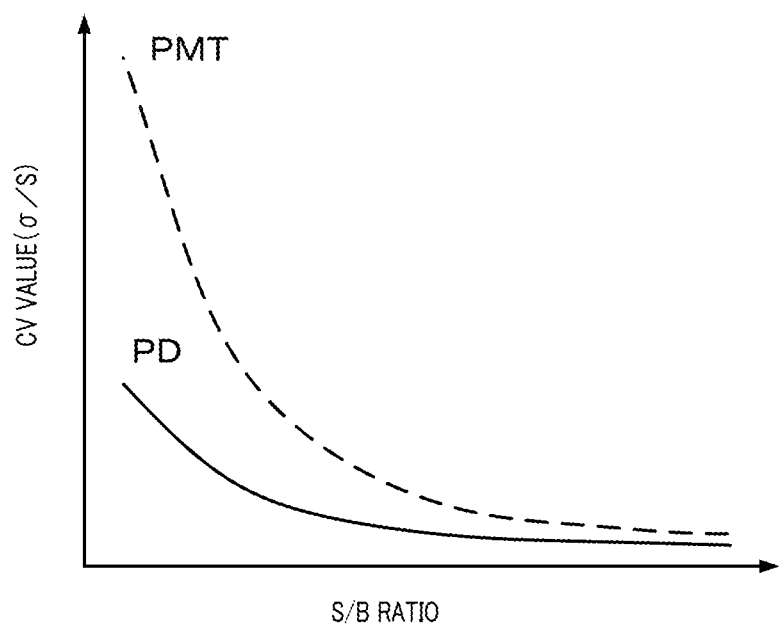

In general, the output value of light receiving sensor 125 is proportional to the light reception amount, the light receiving sensitivity and the amplification multiplying factor. FIGS. 2A and 2B are conceptual graphs showing the detection accuracy of a PMT and a PD. FIG. 2A is a conceptual graph showing a relationship between the output value of light receiving sensor 125 and the standard deviation (non-uniformity) σ of the detection value. FIG. 2B is a conceptual graph showing a relationship between the ratio (SB ratio) of signal value S (S=output value−B, which corresponds to the quantity of fluorescence) obtained by subtracting blank value B from the output value to optical blank value B, and coefficient of variation CV (a ratio (σ/S ratio) of standard deviation σ to signal value S). The range of signal value S in FIG. 2B is a range of the case where standard deviation σ of the PD is smaller than standard deviation σ of the PMT in FIG. 2A. In addition, in FIGS. 2A and 2B, the broken line indicates the PMT, and the solid line indicates the PD.

As illustrated in FIG. 2A, in the case of light receiving sensors having high sensitivity, which include the PMT, standard deviation σ is small when the output value is small, but standard deviation σ increases as the output value increases. Accordingly, coefficient of variation CV (σ/S) does not remarkably decrease even when signal value S increases. In contrast, in the case of light receiving sensors having low sensitivity, which include the PD, standard deviation σ in the region where signal value S is significantly small is large, but, since the increase rate of standard deviation σ is small, coefficient of variation CV exponentially decreases as signal value S increases. In view of this, by increasing signal value S from light receiving sensor 125, it is possible to perform the measurement using the PD with higher accuracy in comparison with the measurement using the PMT.

In addition, in the region where standard deviation σ of the PD is smaller than standard deviation σ of the PMT in FIG. 2A, the increase rate of coefficient of variation CV of the PD is small in comparison with coefficient of variation CV of the PMT even when optical blank value B increases relative to signal value S (or, even when the S/B decreases) as illustrated in FIG. 2B. Accordingly, even when optical blank value B increases relative to signal value S (or, even when the S/B decreases), the accuracy of the measurement using PD is higher than that of the measurement using the PMT.

Since the light receiving sensitivity of a PD is 1/several tens of thousands (for example, 1/50,000) of that of a PMT, the amplification multiplying factor is 1,000 times that of the case where a PMT is used, and the quantity of excitation light α is 20 to 50 times that of the case where a PMT is used in the present embodiment. With this configuration, even when detection is performed with the same detection chip 10, signal value S obtained with the detection using a PMT and signal value S obtained with the detection using a PD are approximately equal to each other. In this manner, by increasing signal value S (output value) such that standard deviation a of the PD is smaller than standard deviation σ of the PMT, it is possible to perform detection using the PD with higher accuracy in comparison with the detection using the PMT.

It is to be noted that the size of the irradiation spot of excitation light α on one surface (the surface that is opposite to facing prism 20) of metal film 30 is adjusted to a size smaller than the size of the detection region of light reception sensor 125 on the other surface (the surface that is opposite to first lens 122) of metal film 30. With such a configuration, it is possible to prevent the irradiation spot from being displaced from the detection region even when the position of the irradiation spot is slightly shifted due to errors of parameters of prism 20.

Control section 130 unitarily performs control of driving sections, quantification of the light reception amount of light reception sensor 125 and the like. In the present embodiment, control section 130 includes light source control section 131 that controls light source unit 111, light receiving sensor control section 132 that controls light receiving sensor 125, and control processing section 133. Control processing section 133 comprehensively controls angle adjusting section 112, light source control section 131, and light reception sensor control section 132 so as to control the entire operation of SPFS device 100. For example, control section 130 is a computer configured to execute software. As described later, control section 130 (control processing section 133) determines a predetermined incident angle (in the present embodiment, an enhancement angle) based on the detection result of plasmon scattering light β of light receiving sensor 125, and controls angle adjusting section 112 to adjust the incident angle of excitation light α to metal film 30 (film formation surface 22) in fluorescence detection.

Chip holder 140 holds detection chip 10 at a predetermined position. Excitation light α from excitation light irradiation unit 110 is applied to detection chip 10 in the state where detection chip 10 is held by chip holder 140. At this time, plasmon scattering light β having a wavelength same as that of excitation light α, fluorescence γ output from the fluorescence material and the autofluorescence of detection chip 10 are emitted upward from the surface of metal film 30 that faces away from prism 20 and from the area in the vicinity of the surface. In addition, excitation light α is reflected by the interface between prism 20 and metal film 30, and emitted to the outside of prism 20 (which is not illustrated in the drawing).

(SPFS Device Detection Operation)

Figure 3:
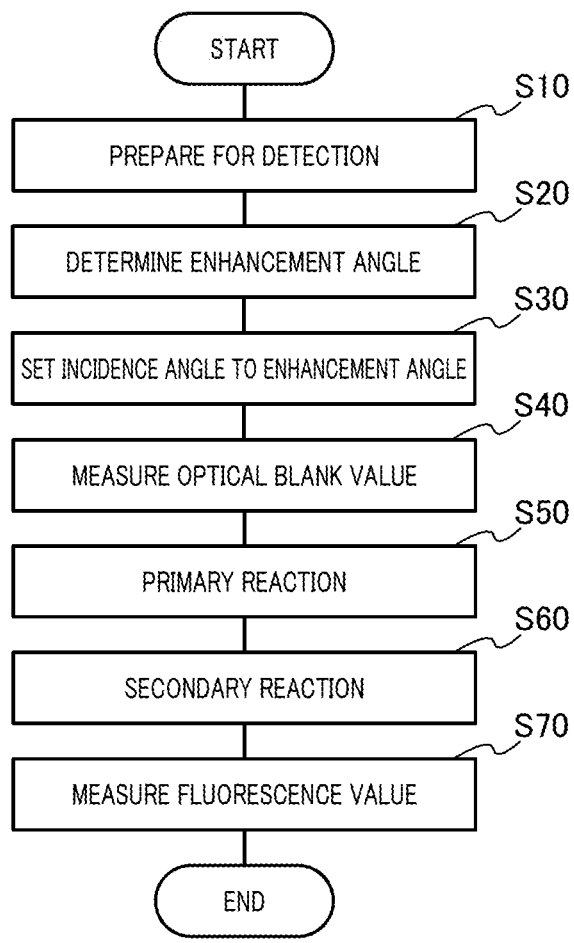
FIG. 3 is a flowchart of an exemplary operation of an SPFS device according to Embodiment 1.

Next, a detection operation of SPFS device 100 is described. FIG. 3 is a flowchart of an exemplary operation of SPFS device 100.

First, preparation for detection is performed (step S10). To be more specific, detection chip 10 is placed at chip holder 140 of SPFS device 100. When a moisturizing agent presents in channel 41 of detection chip 10, the interior of channel 41 is washed to remove the moisturizing agent so that the capturing body can appropriately capture the detection object sub stance.

Next, while applying excitation light α to a predetermined area of metal film 30 (film formation surface 22), the incident angle of excitation light α to metal film 30 (film formation surface 22) is scanned, and an optimum incident angle is determined (step S20). To be more specific, control processing section 133 controls light source unit 111 and angle adjusting section 112 to scan the incident angle of excitation light α to metal film 30 (film formation surface 22) while applying excitation light α to a predetermined area of metal film 30 (film formation surface 22) in the state where no fluorescence material is present on metal film 30. Simultaneously, control processing section 133 controls light receiving sensor control section 132 such that light receiving sensor 125 detects the light (plasmon scattering light β and the autofluorescence of detection chip 10) emitted from detection chip 10. At this time, plasmon scattering light β emitted from detection chip 10 is collimated by first lens 122 and then reaches excitation light cutting filter 123. Excitation light cutting filter 123 allows a part of plasmon scattering light and the autofluorescence of detection chip 10 to pass therethrough. The light having passed through excitation light cutting filter 123 is condensed by second lens 124, and then detected by light receiving sensor 125. In this manner, control processing section 133 obtains data containing a relationship between the incident angle of excitation light α and the intensity of the light emitted from detection chip 10. Then, control processing section 133 analyzes the data by fitting such as quadratic approximation, and determines the incident angle (enhancement angle) at which the intensity of the detected (detection value) is maximized.

While the enhancement angle is basically determined based on the material and the shape of prism 20, the thickness of metal film 30, the refractive index of the liquid in channel 41 and the like, the enhancement angle is also slightly varied by various factors such as the kind and the amount of the capturing body in channel 41, and shaping errors of prism 20. In view of this, it is preferable to determine the enhancement angle for each detection. The enhancement angle is determined in the order of about 0.1 degree.

Next, the incident angle of excitation light α to metal film 30 (film formation surface 22) is set to the enhancement angle determined at step 20 (step S30). To be more specific, control processing section 133 controls angle adjusting section 112 to adjust the incident angle of excitation light α to metal film 30 (film formation surface 22) to the enhancement angle. In the following steps, the incident angle of excitation light α to metal film 30 (film formation surface 22) is maintained at the enhancement angle.

Next, excitation light α is applied to metal film 30 (film formation surface 22), and the intensity (optical blank value) of the light (plasmon scattering light and autofluorescence of detection chip 10) which has passed through excitation light cutting filter 123 is measured (step S40). To be more specific, control processing section 133 controls light source control section 131 such that light source unit 111 emits excitation light α. Simultaneously, control processing section 133 controls light receiving sensor control section 132 such that light receiving sensor 125 detects the light having passed through excitation light cutting filter 123. The measurement value is sent to control processing section 133 and recorded as an optical blank value.

Next, a reaction between the detection object substance in the sample and the capturing body is caused (primary reaction, step S50). To be more specific, a sample is injected into channel 41 of detection chip 10 in the liquid feeding unit side to bring the sample and the capturing body into contact with each other. When the detection object substance is present in the sample, at least a part of the detection object substance is captured by the capturing body. Thereafter, the interior of channel 41 is washed with buffer solution or the like to remove materials which have not been captured by the capturing body. The kind of the sample is not limited. Examples of the sample include bodily fluids such as blood, serum, plasma, urine, nasal mucus, saliva, and semen, and their diluted solutions.

Next, the detection object substance that has been captured by the capturing body is labeled with a fluorescence material (secondary reaction; step S60). To be more specific, a fluorescence labeling solution is injected into channel 41. The fluorescence labeling solution is, for example, a buffer solution containing an antibody (secondary antibody) labeled by a fluorescence material. When the fluorescence labeling solution is injected into channel 41, the fluorescence labeling solution makes contact with the detection object substance, and the detection object substance is labeled with the fluorescence material. Thereafter, the interior of channel 41 is washed with buffer solution and the like to remove the free fluorescence material and the like.

Finally, in the state where the detection object substance labeled with the fluorescence material is present on metal film 30, excitation light α is applied to metal film 30 (film formation surface 22), and fluorescence γ emitted from detection chip 10 is detected to measure the fluorescence value (step S70). To be more specific, control processing section 133 controls light source control section 131 such that light source unit 111 emits excitation light α. Simultaneously, control processing section 133 controls light reception sensor control section 132 such that light reception sensor 125 detects fluorescence γ emitted from metal film 30 (metal film 30 and the area in the vicinity of metal film 30). Control processing section 160 subtracts the optical blank value from the detection value to calculate the intensity of the fluorescence correlating with the amount of the detection object substance. The fluorescence intensity is converted to the amount or the concentration of the detection object substance and the like as necessary.

Through the above-mentioned procedure, the presence or the amount of the detection object substance in the sample can be detected with high accuracy without moving out excitation light cutting filter 123 from the light path of light reception optical system 121.

Now a function of excitation light cutting filter 123 that is used in SPFS device 100 according to the present embodiment and is configured to allow a part of plasmon scattering light β to pass therethrough is described. Here, the following describes a case where the enhancement angle is determined by measuring plasmon scattering light β by use of, as excitation light cutting filter 123, a color glass (whose transmittance of plasmon scattering light β is approximately 0.08%) that allows a part of plasmon scattering light β to pass therethrough. For comparison, the following also describes the case where a high-performance band pass filter (BPF; whose transmittance of plasmon scattering light β is 0.01% or lower) that almost completely block plasmon scattering light β is used as an excitation light cutting filter, and a case where no excitation light cutting filter is used.

Figure 4A:
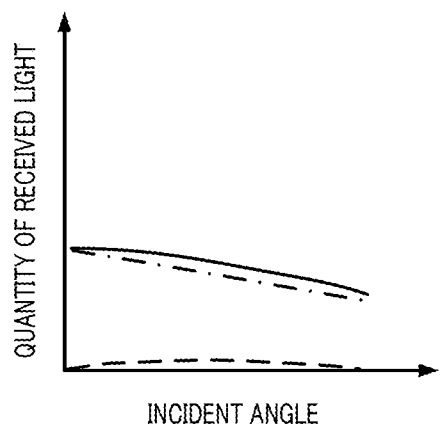
FIGS. 4A to 4C are conceptual graphs for describing a function of an excitation light cutting filter of the SPFS device according to Embodiment 1.
Figure 4B:
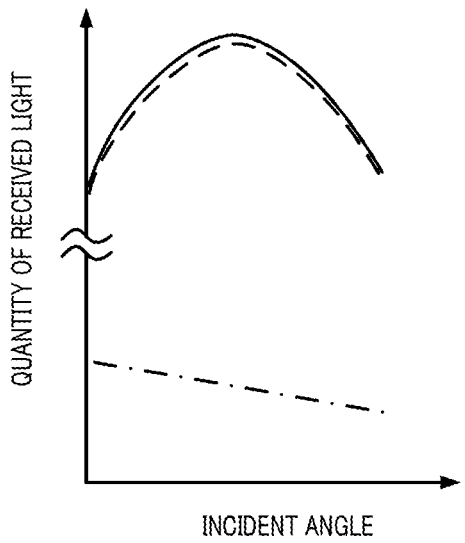
Figure 4C:
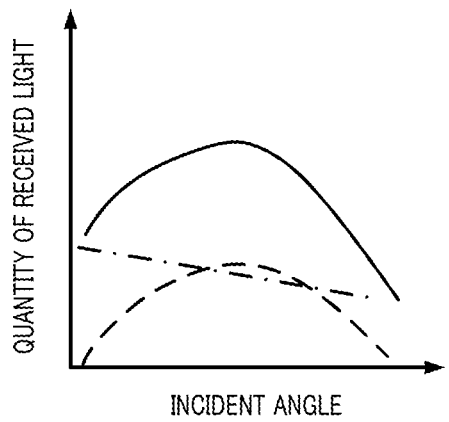

FIGS. 4A to 4C are conceptual graphs for describing a function of excitation light cutting filter 123 in SPFS device 100 according to the present embodiment. FIG. 4A shows a relationship between the incident angle of excitation light α and the light reception amount of light receiving sensor 125 in the case where a high-performance band pass filter (BPF) that almost completely blocks plasmon scattering light β is used as an excitation light cutting filter. FIG. 4B shows a relationship between the incident angle of excitation light α and the light reception amount of light receiving sensor 125 in the case where no excitation light cutting filter is used. FIG. 4C shows a relationship between the incident angle of excitation light α and the light reception amount of light receiving sensor 125 in the case where excitation light cutting filter 123 that allows a part of plasmon scattering light β to pass therethrough is used. In each graph, the incident angle of excitation light α to metal film 30 is scanned in the state where no fluorescence material is present on metal film 30. In FIGS. 4A to 4C, the dashed line indicates the autofluorescence emitted from detection chip 10, the broken line indicates plasmon scattering light β, and the solid line indicates the sum of autofluorescence and plasmon scattering light β.

As shown in FIG. 4A, in the case where the excitation light cutting filter that almost completely blocks plasmon scattering light β is used, the plasmon scattering light β is almost completely blocked, and accordingly the light that reaches light receiving sensor 125 is composed mainly of the autofluorescence emitted from detection chip 10. While the quantity of plasmon scattering light β is largely changed in accordance with the incident angle of excitation light α under the influence of the surface plasmon resonance on light metal film 30 (see the broken line of FIG. 4B), the quantity of autofluorescence is not influenced by the surface plasmon resonance (see the dashed line of FIG. 4A). Accordingly, in the case where the excitation light cutting filter that almost completely blocks plasmon scattering light is used, the variation in the light reception amount of light receiving sensor 125 due to the surface plasmon resonance cannot be detected even when the incident angle of excitation light α is changed (see the solid line of FIG. 4A). As a result, the enhancement angle cannot be properly determined.

On the other hand, as illustrated in FIG. 4B, in the case where no excitation light cutting filter is used, the light that reaches light receiving sensor 125 contains plasmon scattering light β and autofluorescence. At this time, no plasmon scattering light β is blocked by the excitation light cutting filter, and accordingly the quantity of the plasmon scattering light β is far greater than that of the light autofluorescence. In view of this, the enhancement angle can be determined by detecting the incident angle of excitation light α at which the plasmon scattering light β is maximized. With this configuration, however, the detection amount of plasmon scattering light β is approximately 1,000 times or greater the case where the excitation light cutting filter that almost completely blocks plasmon scattering light β is used (see FIG. 4A). Consequently, at step (step S70) of detecting weak fluorescence γ emitted from the fluorescence material that labels the detection object substance, the plasmon scattering light β becomes noise and leads to reduction in S/N ratio.

In view of this, for the purpose of achieving highly accurate detection, in a conventional SPFS device including an excitation light cutting filter that almost completely blocks plasmon scattering light β, plasmon scattering light β is detected in the state where the excitation light cutting filter is moved out from the light path at a step of determining the enhancement angle (step S20), and plasmon scattering light β is detected in the state where the excitation light cutting filter is disposed on the light path to block plasmon scattering light β at a step of detecting fluorescence γ (step S70).

In contrast, in the light emitted from detection chip 10, excitation light cutting filter 123 in SPFS device 100 according to the present embodiment can allow a part of plasmon scattering light β, autofluorescence, and the fluorescence γ emitted from the fluorescence material to pass therethrough. Accordingly, with SPFS device 100 according to the present embodiment, plasmon scattering light β having a suitable quantity that is required for measurement of the enhancement angle, and does not inhibit the detection of fluorescence γ can reach light receiving sensor 125 as illustrated in FIG. 4C. Accordingly, with SPFS device 100 according to the present embodiment, it is not necessary to move out excitation light cutting filter 123 from the light path at the step of determining the enhancement angle (step S20).

At this time, preferably, the transmittance of plasmon scattering light β of excitation light cutting filter 123 is greater than 0.005% and smaller than 1% from the viewpoint of achieving transmission of a suitable quantity of light plasmon scattering light β. In addition, preferably, excitation light cutting filter 123 allows plasmon scattering light β to pass therethrough such that the quantity of plasmon scattering light β is greater than 0.5 times and smaller than 100 times the quantity of the autofluorescence emitted from detection chip 10. The enhancement angle (the maximum value of the quantity of plasmon scattering light β) can be determined by receiving sufficiently intense plasmon scattering light β relative to the autofluorescence, and fluorescence γ can be detected with high accuracy by limiting the transmission quantity of plasmon scattering light β to a degree that does not inhibit the detection of fluorescence γ.

Effect

As described above, SPFS device 100 according to the present embodiment can determine the enhancement angle by utilizing a part of plasmon scattering light β emitted from detection chip 10 which has passed through excitation light cutting filter 123. Accordingly, SPFS device 100 according to the present embodiment can determine the enhancement angle without moving out excitation light cutting filter 123 from the light path of light reception optical system 121. Thus, unlike the conventional SPFS device (see PTL 2), SPFS device 100 according to the present embodiment does not require the mechanism for changing the position of excitation light cutting filter 123, and thus can achieve cost reduction and downsizing of the detection device. In addition, since the step of changing the position of excitation light cutting filter 123 is not required, the detection device according to the present embodiment can shorten the detection time.

In addition, in the present embodiment, the primary reaction (step S50) and the secondary reaction (step S60) are continuously performed, and detection chip 10 is not moved from the liquid feeding unit side to excitation light irradiation unit 110 or light reception unit 120 side in the period between the steps. Thus, the total time required for the detection can be shortened by the time required for moving detection chip 10. In addition, by maintaining the primary reaction time, the secondary reaction time, and the interval between the primary reaction and the secondary reaction constant, the measurement accuracy can be improved. On the other hand, the determination of the enhancement angle (step S20), the setting of the incident angle to the enhancement angle (step S30) and the measurement of optical blank value (step S40) may be performed after the primary reaction (step S50). In this case, while it is necessary to move detection chip 10 in the period between the primary reaction (step S50) and the secondary reaction (step S60), the determination of the enhancement angle and the measurement of the optical blank value can be performed in the state where the detection object substance is captured by the capturing body. As a result, the determination of the enhancement angle and the measurement of the optical blank value can be performed in a state closer to that of the step of measuring the fluorescence value (step S70), and accordingly the determination accuracy of the enhancement angle and the optical blank value can be increased, and, the measurement accuracy can be improved.

Conventionally, to increase the signal value/blank value (S/B) ratio for the purpose of correctly detecting the concentration of a small amount of sample, a method in which a high-performance BPF is used and excitation light α is removed as much as possible, and/or a method using a highly sensitive light receiving sensor (for example, PMT) which can detect weak signals with low noise have been used. In such configurations, however, it is necessary to move out excitation light cutting filter 123 from the light path as described above.

In contrast, in the present embodiment, excitation light cutting filter 123 (for example, a color glass filter) that allows a part of plasmon scattering light β to pass therethrough, and the PD having a lower detection sensitivity than that of the PMT are used. With the configuration in which a part of plasmon scattering light β is transmitted, the S/B ratio is reduced. When the PD is used, however, the increase rate of standard deviation σ of the detection value is low even when the light reception amount is increased in comparison with the case using the PMT. In addition, coefficient of variation CV (σ/S) is small when the light reception amount is large, and increase in coefficient of variation CV can be limited even when the S/B ratio is reduced. As a result, with the PD, the accuracy of the detection can be increased in comparison with the case using the PMT (see FIGS. 2A and 2B).

Embodiment 2

As with SPFS device 100 according to Embodiment 1, SPFS device 200 according to Embodiment 2 includes excitation light irradiation unit 110, light reception unit 220, control section 130 and chip holder 140. SPFS device 200 according to Embodiment 2 is different from SPFS device 100 according to Embodiment 1 only in the configuration of light reception unit 220. Therefore, in the present embodiment, only light reception unit 220 is described.

Figure 5:
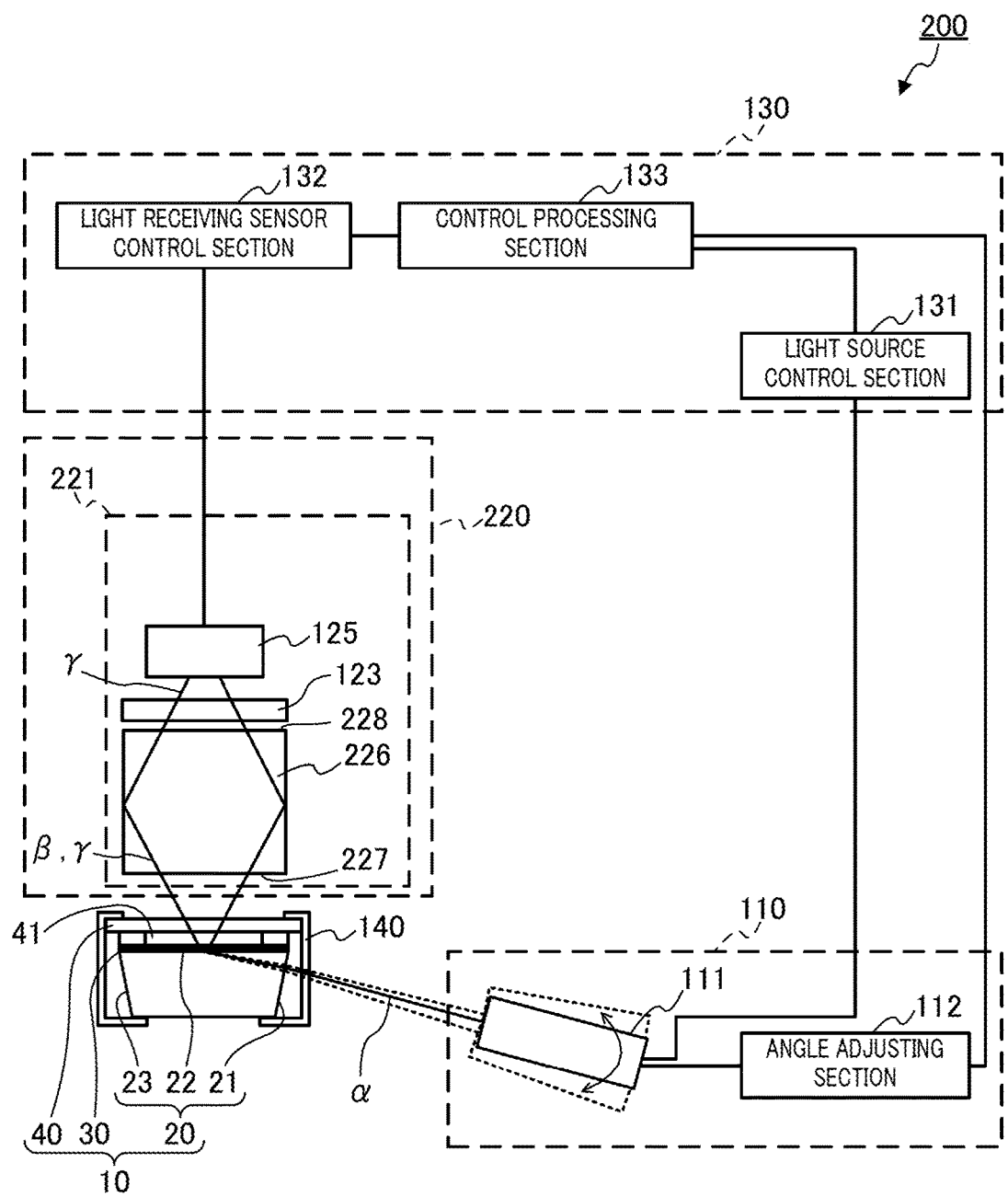
FIG. 5 is a schematic view illustrating a configuration of an SPFS device according to Embodiment 2.

FIG. 5 is a schematic view illustrating a configuration of SPFS device 200 according to Embodiment 2. As illustrated in FIG. 5, light reception unit 220 includes light reception optical system 221 including a light guiding member (light guiding rod 226) and excitation light cutting filter 123, and light receiving sensor 125. Light reception optical system 221 guides the light emitted from detection chip 10 to light receiving sensor 125.

Light guiding rod 226 has light transmissivity, and allows incidence of the light (plasmon scattering light β, fluorescence γ and autofluorescence) emitted from detection chip 10 at incidence surface 227 provided at one end thereof. Light guiding rod 226 emits the light from emission surface 228 provided at the other end thereof and guides the light to light receiving sensor 125.

The shape and the material of light guiding rod 226 is not limited as long as the light emitted from detection chip 10 can be guided to light receiving sensor 125. In the cross-section orthogonal to the axis direction of light guiding rod 226, the shape of light guiding rod 226 may be a columnar shape whose cross-sectional area from incidence surface 227 to emission surface 228 is constant, or a tapered shape whose cross-sectional area from incidence surface 227 to emission surface 228 is not constant. In addition, the shape of incidence surface 227 and emission surface 228 may be a planar shape, or a curved shape. In the present embodiment, light guiding rod 226 has a columnar shape, and each of incidence surface 227 and emission surface 228 has a planar shape. Examples of the material of light guiding rod 226 include a transparent resin and a transparent glass. Preferably, the refractive index of light guiding rod 226 is, but not limited to, about 1.4 to 2.0.

Preferably, the numerical aperture (NA) of light guiding rod 226 is high. With such a configuration, the incident amount of the light emitted from detection chip 10 can be increased.

In addition, a reflection film for preventing leakage of fluorescence γ having entered light guiding rod 226 from incidence surface 227 may be formed on the side surface of light guiding rod 226. The reflection film is, for example, a vapor deposition film of aluminum, gold and the like.

Incidence surface 227 of light guiding rod 226 is one surface (bottom surface) of the column, and disposed to face the surface of metal film 30. The distance between incidence surface 227 of light guiding rod 226 and the detection region of detection chip 10 is about 0.5 to 5.0 mm. The diameter of incidence surface 227 of light guiding rod 226 is larger than the maximum length of the detection region. With this configuration, fluorescence γ emitted from the detection region can efficiently enter light guiding rod 226. The "maximum length of the detection region" is the length of the longest line segment of the line segments whose both ends are two points on the external edge of the detection region. For example, in the case where the detection region has a circular shape, the maximum length of the detection region is the diameter. In the case where the detection region has a rectangular shape, the maximum length of the detection region is the diagonal length.

Emission surface 228 is the other end surface (bottom surface) of the column, and is disposed to face the light reception surface of light receiving sensor 125 (or excitation light cutting filter 123 disposed on the near side). The distance between emission surface 228 and the light reception surface of light receiving sensor 125 is about 0.5 to 5.0 mm. Preferably, the diameter of emission surface 228 of light guiding rod 226 is smaller than the maximum length of the light reception surface of light receiving sensor 125. It is to be noted that the "maximum length of the light reception surface" is the length of the longest line segment of the line segments whose both ends are two points on the external edge of the light reception surface of light receiving sensor 125.

Excitation light cutting filter 123 may be disposed between chip holder 140 and incidence surface 227 of light guiding rod 226, or may be disposed between emission surface 228 of light guiding rod 226 and light receiving sensor 125. In the present embodiment, excitation light cutting filter 123 is disposed between emission surface 228 of light guiding rod 226 and light receiving sensor 125.

Depending on the type, excitation light cutting filter 123 can have incident-angle dependence as the transmission characteristics. For example, in the case of excitation light cutting filter 123 composed of a dielectric multi-layer film, the cut-off wavelength of excitation light cutting filter 123 is changed to the short wavelength side when the incident angle of light beam is greater than 0 degree in comparison with the case where the incident angle of a light beam is 0 degree. Accordingly, in the case where the light beams enter excitation light cutting filter 123 at various incident angles, excitation light cutting filter 123 can allow a part of the incident light. In the present embodiment, the light emitted from emission surface 228 of light guiding rod 226 enters excitation light cutting filter 123 at various incident angles. As a result, by utilizing the incident-angle dependence of the light transmission characteristics of excitation light cutting filter 123, transmission of a suitable quantity of plasmon scattering light β can be achieved. At this time, the quantity of transmitted plasmon scattering light β can be easily set to a suitable quantity by arbitrarily setting the cut-off wavelength of excitation light cutting filter 123 and the NA of the light guiding rod, and by controlling the incident angle range to excitation light cutting filter 123. In view of this, in SPFS device 200 according to the present embodiment, a high-performance BPF may be used as excitation light cutting filter 123. In this case, while the high-performance BPF almost completely blocks plasmon scattering light β which is incident at incident angle of 0 degree and has a wavelength same as the wavelength of excitation light α, it is possible to allow for transmission of light beams whose incident angle is greater than 0 degree by use of light guiding rod 226. Meanwhile, it also is possible to use, as well as high-performance BPFs, inexpensive optical filters such as low performance BPFs whose light shielding rate for excitation light α whose incident angle is 0 degree is low, and absorption filters such as a color glass filter. The absorption filters can easily control the transmittance of plasmon scattering light β by controlling the content of the absorption color and the thickness of the filter.

Effect

As with SPFS device 100 according to Embodiment 1, SPFS device 200 according to the present embodiment can measure the enhancement angle without moving out excitation light cutting filter 123 from the light path of light reception optical system 221 by allowing a part of plasmon scattering light β to pass therethrough. In addition, SPFS device 200 uses light guiding rod 226 and it is not necessary to form a conjugate optical system unlike SPFS device 100 according to Embodiment 1, and therefore further downsizing of the detection device and cost reduction can be achieved. In addition, by using a PD as light receiving sensor 125 and a color glass filter as excitation light cutting filter 123, further downsizing and cost reduction can be achieved.

While light guiding rod 226 and excitation cutting filter 123 are separately provided in the above-mentioned Embodiment 2, excitation light cutting filter 123 and light guiding rod 226 may be integrally provided. For example, light guiding rod 226 and excitation light cutting filter 123 may be integrated to each other by forming a dielectric multi-layer film on incidence surface 227 or emission surface 228 of light guiding rod 226, or light guiding rod 226 may be formed with a material same as the color glass filter. With such configurations, SPFS device 200 can be further downsized and simplified.

This application is entitled to and claims the benefit of Japanese Patent Application No. 2015-053467 filed on Mar. 17, 2015, the disclosure each of which including the specification, drawings and abstract is incorporated herein by reference in its entirety.

INDUSTRIAL APPLICABILITY

The detection device according to the embodiments of the present invention can detect detection object substances with high reliability, and therefore are suitable for laboratory tests and the like, for example.

REFERENCE SIGNS LIST

10 Detection chip
20 Prism
21 Incidence surface (of prism)
22 Film formation surface
23 Emission surface (of prism)
30 Metal film
40 Channel closure
41 Channel
100, 200 SPFS device
110 Excitation light irradiation unit
111 Light source unit
112 Angle adjusting section
120, 220 Light reception unit
121, 221 Light reception optical system
122 First lens
123 Excitation light cutting filter
124 Second lens
125 Light receiving sensor
226 Light guiding rod
227 Incidence surface (of light guiding rod)
228 Emission surface (of light guiding rod)
130 Control section
131 Light source control section
132 Light receiving sensor control section
133 Control processing section
140 Chip holder
α Excitation light
β Plasmon scattering light
γ Fluorescence

The invention claimed is:

1. A detection device configured to, in a state where a detection chip including a prism composed of a dielectric and a metal film disposed on one surface of the prism is placed in the detection device, apply excitation light to the metal film through the prism to excite a fluorescence material for labelling a detection object substance on the metal film with localized light based on surface plasmon resonance, and detect fluorescence emitted from the fluorescence material to detect presence or an amount of the detection object substance, the detection device comprising:
a holder configured to hold the detection chip;
a light irradiation section configured to emit the excitation light;
an angle adjusting section configured to adjust an incident angle of the excitation light to the metal film to apply the excitation light to the metal film through the prism at an optimum incident angle to maximize an intensity of fluorescence light emitted from the detection chip;
a light receiving sensor configured to detect light emitted from the detection chip when the light irradiation section applies the excitation light to the metal film;
a light reception optical system configured to guide the light emitted from the detection chip to the light receiving sensor;
an excitation light cutting filter disposed in the light reception optical system, and configured to block a majority of plasmon scattering light having a wavelength identical to a wavelength of the excitation light; and
a control section configured to control the angle adjusting section, wherein:
the excitation light cutting filter allows fluorescence emitted from the fluorescence material in the light emitted from the detection chip, and an amount of plasmon scattering light that does not inhibit a detection of the fluorescence,
the light receiving sensor detects a part of the plasmon scattering light and auto-fluorescence emitted from the detection chip which has passed through the excitation light cutting filter when the light irradiation section applies the excitation light to the metal film in a state where the fluorescence material is not present on the metal film, on a basis of a detection result of the plasmon scattering light and auto-fluorescence received at the light receiving sensor, wherein the quantity of the plasmon scattering light smaller than 100 times a quantity of the autofluorescence, the control section determines a relationship between an intensity of the received plasmon scattering light and an incident angle, determines the optimum incident angle based on the relationship, and controls the angle adjusting section to adjust an incident angle of the excitation light to the metal film to the optimum incident angle, and the light receiving sensor detects fluorescence emitted from the fluorescence material when the light irradiation section applies the excitation light to the metal film at the predetermined incident angle in a state where the detection object substance labeled with the fluorescence material is present on the metal film such that a surface plasmon resonance is generated on the metal film.

2. The detection device according to claim 1, wherein:

the light emitted from the detection chip further includes autofluorescence of the detection chip; and the excitation light cutting filter allows the plasmon scattering light to pass therethrough such that a quantity of the plasmon scattering light is greater than 0.5 times and smaller than 100 times a quantity of the autofluorescence.

3. The detection device according to claim 1, wherein transmittance of the plasmon scattering light in the excitation light cutting filter is greater than 0.005% and smaller than 1%.

4. The detection device according to claim 1, wherein the light reception optical system includes a light guiding rod configured to allow incidence of the light emitted from the detection chip at an incidence surface provided at one end of the light guiding rod, and emit the light emitted from the detection chip from an emission surface provided at another end of the light guiding rod.

5. The detection device according to claim 1, wherein the light receiving sensor is a photodiode.

6. The detection device according to claim 1, wherein the light irradiation section applies the excitation light such that a power of an irradiated surface on the metal film is 1 mW/mm$^2$ or greater.

7. The detection device according to claim 1, wherein a wavelength of the excitation light emitted by the light irradiation section is 650 to 670 nm.

* * * * *